United States Patent
Lee

(10) Patent No.: US 10,434,070 B2
(45) Date of Patent: Oct. 8, 2019

(54) USE OF NANOPARTICLES COATED WITH RED BLOOD CELL MEMBRANES TO ENABLE BLOOD TRANSFUSION

(71) Applicant: Cellics Therapeutics, Inc., San Diego, CA (US)

(72) Inventor: Tien-Li Lee, San Diego, CA (US)

(73) Assignee: Cellics Therapeutics, Inc., San Diego, CA (US)

( * ) Notice: Subject to any disclaimer, the term of this patent is extended or adjusted under 35 U.S.C. 154(b) by 65 days.

(21) Appl. No.: 15/541,336

(22) PCT Filed: Dec. 21, 2015

(86) PCT No.: PCT/US2015/067209
§ 371 (c)(1),
(2) Date: Jun. 30, 2017

(87) PCT Pub. No.: WO2016/109306
PCT Pub. Date: Jul. 7, 2016

(65) Prior Publication Data
US 2017/0367990 A1  Dec. 28, 2017

Related U.S. Application Data

(60) Provisional application No. 62/099,381, filed on Jan. 2, 2015.

(51) Int. Cl.
| | |
|---|---|
| *A61K 35/18* | (2015.01) |
| *A61K 9/00* | (2006.01) |
| *A61K 9/51* | (2006.01) |
| *A61K 45/06* | (2006.01) |
| *A61K 35/14* | (2015.01) |
| *G01N 33/80* | (2006.01) |
| *A61M 1/02* | (2006.01) |

(52) U.S. Cl.
CPC .......... *A61K 9/5176* (2013.01); *A61K 9/0019* (2013.01); *A61K 9/0026* (2013.01); *A61K 35/14* (2013.01); *A61K 35/18* (2013.01); *A61K 45/06* (2013.01); *G01N 33/80* (2013.01); *A61M 1/02* (2013.01)

(58) Field of Classification Search
None
See application file for complete search history.

(56) References Cited

U.S. PATENT DOCUMENTS

| | | | |
|---|---|---|---|
| 5,358,722 | A | 10/1994 | Monzyk |
| 5,491,219 | A | 2/1996 | Mann |
| 5,653,999 | A | 8/1997 | Gaudreault et al. |
| 6,312,685 | B1 | 11/2001 | Fisher et al. |
| 6,395,029 | B1 | 5/2002 | Levy |
| 9,539,210 | B2 | 1/2017 | Andrian et al. |
| 2004/0110695 | A1 | 6/2004 | Dobbie |
| 2004/0180094 | A1 | 9/2004 | Joyce |
| 2006/0292174 | A1 | 12/2006 | Rios et al. |
| 2007/0243137 | A1 | 10/2007 | Hainfeld |
| 2007/0258889 | A1 | 11/2007 | Douglas et al. |
| 2009/0274630 | A1 | 11/2009 | Huang |
| 2010/0055167 | A1 | 3/2010 | Zhang et al. |
| 2011/0070154 | A1 | 3/2011 | Hyde et al. |
| 2013/0028962 | A1 | 1/2013 | Zhang et al. |
| 2013/0337066 | A1* | 12/2013 | Zhang ............... A61K 39/0011 424/489 |
| 2016/0136106 | A1 | 5/2016 | Zhang et al. |
| 2017/0000875 | A1 | 1/2017 | Hu |
| 2017/0079909 | A1 | 3/2017 | Zhang et al. |
| 2017/0095510 | A1 | 4/2017 | Lee |
| 2017/0274059 | A1 | 9/2017 | Zhang et al. |
| 2018/0085320 | A1 | 3/2018 | Zhang et al. |
| 2018/0140558 | A1 | 5/2018 | Zhang et al. |
| 2018/0153821 | A1 | 6/2018 | Zhang et al. |
| 2018/0169027 | A1 | 6/2018 | Zhang et al. |

FOREIGN PATENT DOCUMENTS

| | | |
|---|---|---|
| WO | 99/00145 A1 | 1/1999 |
| WO | 2010014081 A1 | 2/2010 |
| WO | 2010070620 A1 | 6/2010 |
| WO | 2011002239 A2 | 1/2011 |
| WO | 2013/052167 A2 | 4/2013 |
| WO | 2017/087897 A1 | 5/2017 |

OTHER PUBLICATIONS

Copp et al., , Proc. Natl. Acad. Sci. U.S.A. 2014, 111:13481-13486 (Year: 2014).*
Hu et al., Nat. Nanotechnol. 2013, 8: 336-340 (Year: 2013).*
US, Office Action for U.S. Appl. No. 13/827,906, dated Aug. 20, 2014, 16 pages.
US, Response to Office Action for U.S. Appl. No. 13/827,906, dated Feb. 20, 2015, 15 pages.
US, Office Action for U.S. Appl. No. 13/827,906, dated Feb. 17, 2016, 20 pages.
US, Response to Office Action for U.S. Appl. No. 13/827,906, dated Aug. 15, 2016, 74 pages.
US, Office Action for U.S. Appl. No. 13/827,906, dated Feb. 27, 2017, 19 pages.
US, Response to Office Action for U.S. Appl. No. 13/827,906, dated May 30, 2017, 21 pages.
US, Office Action for U.S. Appl. No. 13/827,906, dated Nov. 30, 2017, 14 pages.
US, Response to Office Action for U.S. Appl. No. 13/827,906, dated May 30, 2018, 14 pages.
US, Cited list for U.S. Appl. No. 13/827,906, dated, Nov. 30, 2017, 1 page.

(Continued)

*Primary Examiner* — Daniel C Gamett
(74) *Attorney, Agent, or Firm* — Rimon, P.C.

(57) ABSTRACT

The present invention relates to methods, combinations and pharmaceutical compositions for supplying a blood source from a donor source with a mis-matched blood type, or potentially a mis-matched blood type, to a recipient, using, inter alia, an effective amount of a nanoparticle comprising a) an inner core comprising a non-cellular material, and b) an outer surface comprising a cellular membrane derived from a red blood cell, the cellular membrane of the nanoparticle comprising a blood type antigen that exists on the red blood cell from the donor source, but is missing or potentially missing on red blood cells of the recipient.

21 Claims, No Drawings

(56) References Cited

OTHER PUBLICATIONS

Written Opinion for patent application PCT/US2015/067209, dated Mar. 11, 2016, 7 pages.
International Search Report for patent application PCT/US2015/067209, dated Mar. 11, 2016, 3 pages.
International preliminary report for patent application PCT/US2015/067209, dated Jul. 4, 2017, 8 pages.
Written Opinion for patent application PCT/US2015/033366, dated Sep. 2, 2015, 7 pages.
International Search Report for patent application PCT/US2015/033366, dated Sep. 2, 2015, 3 pages.
International Preliminary Report on Patentability for patent application PCT/US2015/033366, dated Dec. 6, 2016, 8 pages.
Written Opinion of the International Searching Authority for patent application PCT/US2012/039411, dated Apr. 8, 2013, 4 pages.
International Search Report for patent application PCT/US2012/039411, dated Apr. 8, 2013, 3 pages.
International Preliminary Report for patent application PCT/US2012/039411, dated Mar. 25, 2014, 5 pages.
Written Opinion of the International Searching Authority for patent application PCT/US15/46016, dated Dec. 4, 2015, 7 pages.
International Search Report for patent application PCT/US15/46016, dated Dec. 4, 2015, 3 pages.
International Preliminary Report for patent application PCT/US15/046016, dated Feb. 21, 2017, 8 pages.
US, Office Action for U.S. Appl. No. 15/505,148, dated Feb. 7, 2019, 7 pages.
US, List of References by examiner for U.S. Appl. No. 15/315,709, dated Dec. 14, 2018, 1 page.
Hu et al. "Marker-of-self functionalization of nanoscale particles through a top-down cellular membrane coating approach," Nanoscale, Apr. 7, 2013, 5(7), P: 2664-2668 https://www.ncbi.nlm.nih.gov/pmc/articles/PMC3667603/.
Hu et al. "Erythrocyte membrane-camouflaged polymeric nanoparticles as a biomimetic delivery platform," Proceedings of the National Academy of Sciences, Jul. 5, 2011. vol. 108. No. 27, P.10980-10985 www.pnas.org/cgi/doi/10.1073/pnas.1106634108.
Yoo et al. "In vitro and in vivo anti-tumor activities of nanoparticles based on doxorubicin-PLGA conjugates," Journal of Controlled Release, Sep. 3, 2000, vol. 68, Issue 3, pp. 419-431 https://doi.org/10.1016/S0168-3659(00)00280-7.
Gao et al. "Modulating Antibacterial Immunity via Bacterial Membrane-Coated Nanoparticles," Nano Lett. 2015, 15, P:1403-1409 DOI: 10.1021/nl504798g.
Hu et al. "Nanoparticle biointerfacing by platelet membrane cloaking," Nature, vol. 526, P:118, Oct. 1, 2015 d oi: 10.1038/nature15373.
Fang et al. "Cancer Cell Membrane-Coated Nanoparticles for Anticancer Vaccination and Drug Delivery," Nano Lett. 2014, 14, 2181-2188, dx.doi.org/10.1021/nl500618u.
Some Definitions of Constituent by Merriam-Webster, http://www.merriam-webster.com/dictionary/constituent, Aug. 15, 2016.
US, Office Action for U.S. Appl. No. 13/827,906, dated Apr. 9, 2019, 17 pages.

* cited by examiner

US 10,434,070 B2

USE OF NANOPARTICLES COATED WITH RED BLOOD CELL MEMBRANES TO ENABLE BLOOD TRANSFUSION

I. CROSS REFERENCES TO RELATED APPLICATION

This application is the national phase of PCT application PCT/US2015/067209 having an international filing date of Dec. 21, 2015, which claims priority to U.S. Provisional Patent Application No. 62/099,381, filed Jan. 2, 2015. The contents of the above-referenced applications are incorporated by reference herein in their entireties for all purposes.

II. FIELD OF THE INVENTION

The present invention relates to methods, combinations and pharmaceutical compositions for supplying a blood source with a mis-matched blood type, or potentially a mis-matched blood type, to a recipient.

III. BACKGROUND OF THE INVENTION

Approximately 85 million units of red blood cells are transfused each year worldwide; over 15 million pints of blood are transfused annually in the U.S. and Canada. Blood transfusions are common, with approximately 1 in 7 hospitalized patients requiring at least one transfusion.

In the United States, blood transfusion may be the most common procedure performed for patients 45 years of age and older (in 2011), and among the top five most common procedures for patients between the ages of 1 and 44 years. Although most transfusions are conducted without major complications, transfusion related adverse events cost approximately $17 Billion/year in the U.S. which account for more of the cost of each transfusion than acquisition and procedure costs combined. See e.g., Shander, A; Hofmann, A; Gombotz, H; Theusinger, O M; Spahn, D R (2007). "Estimating the cost of blood: Past, present, and future directions". *Best practice & research. Clinical anaesthesiology* 21 (2): 271-89.

In order to transfuse blood safely to a patient, one normally must make sure the donor blood is compatible with the recipient. Otherwise transfusion reactions may occur which often result from antibodies in the recipient attacking antigens on the donor blood cells, which can result in the red blood cell hemolysis leading to fever, hypotension, acute respiratory failure, and acute renal failure. However, under certain circumstances, blood type information of the donor and/or the recipient may not be known before a blood source must be supplied to a recipient, or sufficiently amount of a blood supply with a matching blood type is not available. In such circumstances, the patient must go without blood, or the clinician must weigh the cost/benefit of purposely supplying or transfusing a blood supply with a mis-matched blood type, or potentially a mis-matched blood type, to a recipient.

Therefore, what are needed are methods and/or compositions that enable supplying or transfusing a blood supply with a mis-matched blood type, or potentially a mis-matched blood type, to a recipient while reducing, minimizing or removing the adverse effects caused by or associated with such blood supplying or transfusing to a recipient. The present invention addresses these and other related needs in the art.

IV. SUMMARY OF THE INVENTION

In one aspect, the present invention provides for a method for supplying a blood source to a recipient, which method comprise supplying a blood source comprising red blood cells from a donor source to a recipient in need of said supplied blood source, wherein: the blood type of said recipient is unknown before receiving said blood source that potentially has a mis-matched blood type, or the blood type of said recipient is known and is a mis-match to the blood type of said blood source, and before, during, or after supplying said blood source to said recipient, supplying to said recipient an effective amount of a nanoparticle comprising a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient.

In another aspect, the present invention is directed to an use of an effective amount of a nanoparticle for the manufacture of a medicament to be supplied to a recipient in need of receiving a blood source comprising red blood cells from a donor source, wherein: the blood type of said recipient is unknown before receiving said blood source that potentially has a mis-matched blood type, or the blood type of said recipient is known and is a mis-match to the blood type of said blood source, said nanoparticle comprises a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient, and said effective amount of a nanoparticle is configured to be supplied to said recipient before, during, or after said blood source is supplied to said recipient.

In still another aspect, the present invention provides for a combination for supplying a blood source to a recipient, which combination comprises an effective amount of a nanoparticle and an effective amount of a blood source comprising red blood cells from a donor source, wherein the blood type of said recipient is unknown before receiving said blood source that potentially has a mis-matched blood type, or the blood type of said recipient is known and is a mis-match to the blood type of said blood source, said nanoparticle comprises a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient, and said effective amount of a nanoparticle is configured to be supplied to said recipient before, during, or after said blood source is supplied to said recipient. The present invention also provides for a pharmaceutical composition comprising the combination and a method for supplying a blood source to a recipient using the combination or the pharmaceutical composition comprising the combination.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties. The nanoparticles used in the present methods and compositions can be prepared by any suitable processes. For example, the nanoparticles used in the present methods and compositions can be prepared by any suitable processes disclosed in U.S. application Ser. No.

13/827,906, International Application No. PCT/US2012/039411, and/or U.S. provisional application Ser. No. 61/492,626.

V. DETAILED DESCRIPTION OF THE INVENTION

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, $2^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy*, $20^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Supplying a Blood Source to a Recipient

In one aspect, the present invention provides for a method for supplying a blood source to a recipient, which method comprise supplying a blood source comprising red blood cells from a donor source to a recipient in need of said supplied blood source, wherein: the blood type of said recipient is unknown before receiving said blood source that potentially has a mis-matched blood type, or the blood type of said recipient is known and is a mis-match to the blood type of said blood source, and before, during, or after supplying said blood source to said recipient, supplying to said recipient an effective amount of a nanoparticle comprising a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient.

The present methods can be used for supplying any suitable types of blood source to a recipient. In some embodiments, the blood source can comprise whole blood from a donor source. In other embodiments, the blood source can comprise red blood cells from a donor source and the white blood cells, clotting factors and/or platelets from the donor source can be removed. In still other embodiments, the blood source can comprise isolated red blood cells from a donor source.

The present methods can be used for supplying a blood source from any suitable donor to any suitable recipient. In some embodiments, the recipient and the donor can be from different species and the cellular membrane of the nanoparticle can be derived from a red blood cell of a subject that is the same species of the donor. For example, the recipient is a human and the donor is a non-human animal, e.g., a non-human mammal, and the cellular membrane of the nanoparticle is derived from a red blood cell of a subject that is the same species of the non-human animal, e.g., the non-human mammal. In another example, the recipient is a non-human animal, e.g., a first non-human mammal, and the donor is another species of non-human animal, e.g., a second, different species of non-human mammal, and the cellular membrane of the nanoparticle is derived from a red blood cell of a subject that is the same species of the second, different species of non-human mammal.

In other embodiments, the recipient and the donor can be from the same species, and the cellular membrane of the nanoparticle can be derived from a red blood cell of a subject that is the same species of the recipient and the donor. For example, the recipient is a first human and the donor is a second human, and the cellular membrane of the nanoparticle is derived from a red blood cell of a human, e.g., the second human. In another example, the recipient is a non-human animal, e.g., a non-human mammal, the donor is the same species of the non-human animal, and the cellular membrane of the nanoparticle is derived from a red blood cell of a subject that is the same species of the non-human animal.

The blood source can be supplied to the recipient by any suitable routes or methods. In some embodiments, the blood source can be supplied to the recipient's circulation intravenously.

In some embodiments, the blood type of the recipient can be unknown before receiving the blood source that potentially has a mis-matched blood type. This may be the case when it is impossible or impractical to determine the blood type of a recipient before a blood source has to be supplied to the recipient. For example, in some cases, a recipient is in a medical emergency or other life-threatening situation and there is not enough time for determining the blood type of the recipient before a blood source has to be supplied to the recipient. In another example, a recipient is in an environment wherein there is no tools or reagents needed to determine the blood type of a recipient before a blood source has to be supplied to the recipient.

In some embodiments, the blood type of the recipient is known and there is a mis-match to the blood type of the blood source. For example, a recipient is in a medical emergency or other life-threatening situation and a blood source with the matching blood type is not available, or not available at a sufficient amount or volume. In this case, a blood source with the mis-matching blood type has to be supplied to the recipient.

The nanoparticle can be supplied to a recipient at any suitable time relative to the time when the blood source is supplied to the recipient. In some embodiments, the nanoparticle can be supplied to a recipient before the blood source is supplied to the recipient. In other embodiments, the nanoparticle can be supplied to a recipient during the time when the blood source is supplied to the recipient. In still other embodiments, the nanoparticle can be supplied to a recipient after the blood source is supplied to the recipient.

The cellular membrane of the nanoparticle can comprise any suitable blood type antigen that is missing or potentially missing on red blood cells of the recipient. In some embodiments, the cellular membrane of the nanoparticle can comprise a blood type antigen in a major blood group system that is missing or potentially missing on red blood cells of the recipient. For example, the major blood group system can be the ABO blood group system and the blood type antigen can be the antigen that determines the A blood type, B blood type or AB blood type. In another example, the major blood group system can be the Rh blood group system. In still another example, the blood type antigen that is missing or potentially missing on red blood cells of the recipient can be antigen D, C, c, E, or e. In other embodiments, the cellular membrane of the nanoparticle can comprise a blood type antigen in a minor or rare blood group system that is missing or potentially missing on red blood cells of the recipient.

In some embodiments, the cellular membrane of the nanoparticle comprises a blood type antigen in a blood group system including ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, At$^a$ Antigen, AnWj antigen, Sd$^a$ Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. The nanoparticles can be used to enable blood supply or transfusion to a recipient whose red blood cells lack or potentially lack the corresponding blood type antigen in a blood group system such as the ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, At$^a$ Antigen, AnWj antigen, Sd$^a$ Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. For example, the red blood cells of the recipient lack or potentially lack the Vel antigen and the cellular membrane of the nanoparticle comprises the Vel antigen. In some embodiments, the cellular membrane of the nanoparticle comprises a blood type antigen in a blood group system listed in the following Table 1.

TABLE 1

Exemplary blood group systems

| No. | System name | System symbol | Gene name(s)* | Chromosomal location | CD numbers |
|-----|-------------|---------------|---------------|---------------------|------------|
| 001 | ABO | ABO | ABO | 9q34.2 | |
| 002 | MNS | MNS | GYPA, GYPB, GYPE | 4q31.21 | CD235 |
| 003 | P1PK | P1PK | A4GALT | 22q13.2 | |
| 004 | Rh | RH | RHD, RHCE | 1p36.11 | CD240 |
| 005 | Lutheran | LU | LU | 19q13.32 | CD239 |
| 006 | Kell | KEL | KEL | 7q34 | CD238 |
| 007 | Lewis | LE | FUT3 | 19p13.3 | |
| 008 | Duffy | FY | DARC | 1q23.2 | CD234 |
| 009 | Kidd | JK | SLC14A1 | 18q12.3 | |
| 010 | Diego | DI | SLC4A1 | 7q21.31 | CD233 |
| 011 | Yt | YT | ACHE | 7q22.1 | |
| 012 | Xg | XG | XG, MIC2 | Xp22.33 | CD99† |
| 013 | Scianna | SC | ERMAP | 1p34.2 | |
| 014 | Dombrock | DO | ART4 | 12p12.3 | CD297 |
| 015 | Colton | CO | AQP1 | 7p14.3 | |
| 016 | Landsteiner-Wiener | LW | ICAM4 | 19p13.2 | CD242 |
| 017 | Chido/Rodgers | CH/RG | C4A, C4B | 6p21.3 | |
| 018 | H | H | FUT1 | 19q13.33 | CD173 |
| 019 | Kx | XK | XK | Xp21.1 | |
| 020 | Gerbich | GE | GYPC | 2q14.3 | CD236 |
| 021 | Cromer | CROM | CD55 | 1q32.2 | CD55 |
| 022 | Knops | KN | CR1 | 1q32.2 | CD35 |
| 023 | Indian | IN | CD44 | 11p13 | CD44 |
| 024 | Ok | OK | BSG | 19p13.3 | CD147 |
| 025 | Raph | RAPH | CD151 | 11p15.5 | CD151 |
| 026 | John Milton Hagen | JMH | SEMA7A | 15q24.1 | CD108 |
| 027 | I | I | GCNT2 | 6p24.2 | |
| 028 | Globoside | GLOB | B3GALT3 | 3q26.1 | |
| 029 | Gill | GIL | AQP3 | 9p13.3 | |
| 030 | Rh-associated glycoprotein | RHAG | RHAG | 6p21-qtcr | CD241 |
| 031 | FORS | FORS | GBGT1 | 9q34.13 | |
| 032 | JR | JR | ABCG2 | 4q22 | |
| 033 | LAN | LAN | ABCB6 | 2q36 | |

*As recognized by the HUGO Gene Nomenclature Committee
http://www.genenames.org/

The present methods can be used in any suitable manner or for any suitable purpose. In some embodiments, the present methods can be used to supply a blood source to a recipient when the blood type of the recipient is unknown and it is impractical or impossible to determine the blood type of the recipient before supplying the blood source that potentially has a mis-matched blood type. In other embodiments, the present methods can be used to supply a blood source to a recipient when the blood type of the recipient is known and the blood source that has a mis-matched blood type is supplied to the recipient because there is not sufficient supply of a blood source that has a matched blood type.

The present methods can be used to minimize or prevent an immunologic reaction of the recipient against the red blood cells from the donor source. In some embodiments, the present methods can be used to minimize or prevent an immunologic reaction of the recipient against the red blood cells from the donor source that is mediated by the antibodies of the recipient against the red blood cells from the donor source. In other embodiments, the present methods can be used to minimize or prevent hemolysis in the recipient due to supplying the blood source that has a mis-matched blood type to the recipient. For example, the present methods can be used to minimize or prevent hemolysis that is associated with an acute hemolytic transfusion reaction (AHTR). In another example, the present methods can be used to minimize or prevent hemolysis that is associated with a delayed hemolytic reaction.

The present methods can be used to supply a blood source to a recipient when the recipient's hemoglobin level indicates that it is necessary or desirable to supply a blood source to a recipient. In some embodiments, the present methods can be used to supply a blood source to a recipient when the recipient's hemoglobin level falls below about 10 g/dL or hematocrit falls below about 30%. In other embodiments, the present methods can be used to supply a blood source to a recipient when the recipient's hemoglobin level falls below about 7-8 g/dL.

The present methods can further comprise conducting a blood type compatibility test between a blood sample of the recipient and the blood source in the presence and absence of the nanoparticle to assess the efficacy of the nanoparticle for minimizing or preventing an immunologic reaction of the recipient against the red blood cells from the donor source. Any suitable blood type compatibility test can be conducted. In some embodiments, the blood type compatibility test can be conducted between a serum of the recipient and the red blood cells of the blood source. In other embodiments, the blood type compatibility test can be conducted using an immediate spin method or a full cross-matching test. In still some embodiments, the blood type of the recipient is unknown and the present methods further comprises, after supplying the blood source to the recipient, conducting a blood type compatibility test between a blood sample of the recipient and the blood source to assess whether the blood type of the recipient matches with the blood type of the blood source.

The present methods can be used to supply a blood source to any suitable recipient. In some embodiments, the recipient can be a pediatric patient, a pregnant woman, a person with massive trauma, a person who needs massive blood transfusion, a person who needs frequent blood transfusion, a person with a medical emergency, a person in a surgical procedure, a person in a war zone, an accident, a remote area, an epidemic, or a pandemic. In other embodiments, the present methods can be conducted for veterinary use. For example, the present methods can be used to supply a blood source to a recipient that is a pet, a farm animal or an economic animal. In another example, the present methods can be used to supply a blood source to a recipient that is a cat, a cattle, a dog, a pig or a horse.

The present methods can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, e.g., a plasma membrane derived from a human red blood cell. In some embodiments, The nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell.

The present methods can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the recipient or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. In another example, the releasable cargo can be a metallic particle, a polymeric particle, a dendrimer particle, or an inorganic particle. In still another example, the releasable cargo can be an agent that facilitates blood supply or transfusion to the recipient. For example, the releasable cargo can be an agent that treats hemolysis or autoimmune reactions such as Rituximab, folate (which is depleted with hemolysis), a corticosteroid, e.g., prednisone, or an iron salt.

The nanoparticle can have any suitable size. For example, the nanoparticle can have a diameter from about 10 nm to about 10 µm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the red blood cell from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the red blood cell from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the donor's red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for facilitating or enabling blood supply or transfusion to the recipient.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35, or 40 hours.

In some embodiments, the outer surface of the nanoparticle can further comprise a synthetic membrane.

In some embodiments, the nanoparticle substantially lacks immunogenicity to the recipient. For example, the cellular membrane can be derived from a red blood cell from the same species of the recipient. In another example, the recipient is a human and the cellular membrane is derived from a human red blood cell.

The present methods can further comprise administering another active ingredient to the recipient. The other active ingredient can be used for any suitable purposes. In some embodiments, the other active ingredient can be used to facilitate or enable blood supply or transfusion to the recipient. For example, the other active ingredient can be used to treat, prevent or manage the hemolysis associated with an acute hemolytic transfusion reaction (AHTR) in the recipient. In another example, the other active ingredient can be used to treat, prevent or manage the hemolysis associated with a delayed hemolytic reaction in the recipient. In still another example, the other active ingredient can be used to treat, prevent or manage hemolysis or autoimmune reactions, such as Rituximab, folate (which is depleted with hemolysis), a corticosteroid, e.g., prednisone, or an iron salt. In other embodiments, the other active ingredient can be used to treat or prevent a disease or condition in the recipient, e.g., a disease or condition unrelated to the blood supply or transfusion to the recipient.

In some embodiments, the present methods can further comprise administering a pharmaceutically acceptable carrier or excipient to the recipient.

The nanoparticle can be administered using any suitable delivery mechanisms or techniques. In some embodiments, the nanoparticle can be administered alone. In other embodiments, the nanoparticle can be administered with a pharmaceutically acceptable carrier or excipient. In still other embodiments, the nanoparticle can be administered via a medicament delivery system.

The nanoparticle, alone or in combination with other active ingredient(s), can be administered via any suitable administration routes. In some embodiments, the nanoparticle, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

C. Use of an Effective Amount of a Nanoparticle for the Manufacture of a Medicament for Supplying a Blood Source to a Recipient In another aspect, the present invention is directed to an use of an effective amount of a nanoparticle for the manufacture of a medicament to be supplied to a recipient in need of receiving a blood source comprising red blood cells from a donor source, wherein: the blood type of said recipient is unknown before receiving said blood source that potentially has a mis-matched blood type, or the blood type of said recipient is known and is a mis-match to the blood type of said blood source, said nanoparticle comprises a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient, and said effective amount of a nanoparticle is configured to be supplied to said recipient before, during, or after said blood source is supplied to said recipient.

The manufactured medicament can be used for supplying any suitable types of blood source to a recipient. In some embodiments, the blood source can comprise whole blood from a donor source. In other embodiments, the blood source can comprise red blood cells from a donor source and the white blood cells, clotting factors and/or platelets from the donor source can be removed. In still other embodiments, the blood source can comprise isolated red blood cells from a donor source.

The manufactured medicament can be used for supplying a blood source from any suitable donor to any suitable recipient. In some embodiments, the recipient and the donor can be from different species and the cellular membrane of the nanoparticle can be derived from a red blood cell of a subject that is the same species of the donor. For example, the recipient is a human and the donor is a non-human animal, e.g., a non-human mammal, and the cellular membrane of the nanoparticle is derived from a red blood cell of a subject that is the same species of the non-human animal, e.g., the non-human mammal. In another example, the recipient is a non-human animal, e.g., a first non-human mammal, and the donor is another species of non-human animal, e.g., a second, different species of non-human mammal, and the cellular membrane of the nanoparticle is derived from a red blood cell of a subject that is the same species of the second, different species of non-human mammal.

In other embodiments, the recipient and the donor can be from the same species, and the cellular membrane of the nanoparticle can be derived from a red blood cell of a subject that is the same species of the recipient and the donor. For example, the recipient is a first human and the donor is a second human, and the cellular membrane of the nanoparticle is derived from a red blood cell of a human, e.g., a second human. In another example, the recipient is a non-human animal, e.g., a non-human mammal, the donor is the same species of the non-human animal, and the cellular membrane of the nanoparticle is derived from a red blood cell of a subject that is the same species of the non-human animal.

The manufactured medicament can be configured for supplying a blood source to a recipient via any suitable routes or methods. In some embodiments, the manufactured medicament can be configured for supplying a blood source to a recipient's circulation intravenously.

The manufactured medicament can be used in any suitable way to facilitate or enable supplying a blood source to a recipient. In some embodiments, the blood type of the recipient can be unknown before receiving the blood source that potentially has a mis-matched blood type. This may be the case when it is impossible or impractical to determine the blood type of a recipient before a blood source has to be supplied to the recipient. For example, in some cases, a recipient is in a medical emergency or other life-threatening situation and there is not enough time for determining the blood type of the recipient before a blood source has to be supplied to the recipient. In another example, a recipient is in an environment wherein there is no tools ore reagents needed to determine the blood type of a recipient before a blood source has to be supplied to the recipient.

In some embodiments, the blood type of the recipient is known and there is a mis-match to the blood type of the blood source. For example, a recipient is in a medical emergency or other life-threatening situation and a blood source with the matching blood type is not available, or not available at a sufficient amount or volume. In this case, a blood source with the mis-matching blood type has to be supplied to the recipient.

The manufactured medicament comprising the nanoparticle can be supplied to a recipient at any suitable time relative to the time when the blood source is supplied to the recipient. In some embodiments, the manufactured medicament comprising the nanoparticle can be supplied to a recipient before the blood source is supplied to the recipient. In other embodiments, the manufactured medicament comprising the nanoparticle can be supplied to a recipient during the time when the blood source is supplied to the recipient. In still other embodiments, the manufactured medicament comprising the nanoparticle can be supplied to a recipient after the blood source is supplied to the recipient.

The cellular membrane of the nanoparticle in the manufactured medicament can comprise any suitable blood type antigen that is missing or potentially missing on red blood cells of the recipient. In some embodiments, the cellular membrane of the nanoparticle can comprise a blood type antigen in a major blood group system that is missing or potentially missing on red blood cells of the recipient. For example, the major blood group system can be the ABO blood group system and the blood type antigen can be the antigen that determines the A blood type, B blood type or AB blood type. In another example, the major blood group system can be the Rh blood group system. In still another example, the blood type antigen that is missing or potentially missing on red blood cells of the recipient can be antigen D, C, c, E, or e. In other embodiments, the cellular membrane of the nanoparticle can comprise a blood type antigen in a minor or rare blood group system that is missing or potentially missing on red blood cells of the recipient.

In some embodiments, the cellular membrane of the nanoparticle in the manufactured medicament comprises a blood type antigen in a blood group system including ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, At$^a$ Antigen, AnWj antigen, Sd$^a$ Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. The manufactured medicament comprising the nanoparticles can be used to enable blood supply or transfusion to a recipient whose red blood cells lack or potentially lack the corresponding blood type antigen in a blood group system such as the ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, At$^a$ Antigen, AnWj antigen, Sd$^a$ Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. For example, the red blood cells of the recipient lack or potentially lack the Vel antigen and the cellular membrane of the nanoparticle comprises the Vel antigen. In some embodiments, the cellular membrane of the nanoparticle comprises a blood type antigen in a blood group system listed in the Table 1 set forth in the above Section IV.B.

The present manufactured medicament can be used in any suitable manner or for any suitable purpose. In some embodiments, the present manufactured medicament can be used to supply a blood source to a recipient when the blood type of the recipient is unknown and it is impractical or impossible to determine the blood type of the recipient before supplying the blood source that potentially has a mis-matched blood type. In other embodiments, the present manufactured medicament can be used to supply a blood source to a recipient when the blood type of the recipient is known and the blood source that has a mis-matched blood type is supplied to the recipient because there is not sufficient supply of a blood source that has a matched blood type.

The present manufactured medicament can be used to minimize or prevent an immunologic reaction of the recipient against the red blood cells from the donor source. In some embodiments, the present manufactured medicament can be used to minimize or prevent an immunologic reaction of the recipient against the red blood cells from the donor source that is mediated by the antibodies of the recipient against the red blood cells from the donor source. In other embodiments, the present manufactured medicament can be used to minimize or prevent hemolysis in the recipient due to supplying the blood source that has a mis-matched blood type to the recipient. For example, the present manufactured medicament can be used to minimize or prevent hemolysis that is associated with an acute hemolytic transfusion reaction (AHTR). In another example, the present manufactured medicament can be used to minimize or prevent hemolysis that is associated with a delayed hemolytic reaction.

The present manufactured medicament can be used to supply a blood source to a recipient when the recipient's hemoglobin level indicates that it is necessary or desirable to supply a blood source to a recipient. In some embodiments, the present manufactured medicament can be used to supply a blood source to a recipient when the recipient's hemoglobin level falls below about 10 g/dL or hematocrit falls below about 30%. In other embodiments, the present manufactured medicament can be used to supply a blood source to a recipient when the recipient's hemoglobin level falls below about 7-8 g/dL.

The present manufactured medicament can be used to supply a blood source to any suitable recipient. In some embodiments, the recipient can be a pediatric patient, a pregnant woman, a person with massive trauma, a person who needs massive blood transfusion, a person who needs frequent blood transfusion, a person with a medical emergency, a person in a surgical procedure, a person in a war zone, an accident, a remote area, an epidemic, or a pandemic. In other embodiments, the present manufactured medicament can be configured for veterinary use. For example, the present manufactured medicament can be used to supply a blood source to a recipient that is a pet, a farm animal or an economic animal. In another example, the present manufactured medicament can be used to supply a blood source to a recipient that is a cat, a cattle, a dog, a pig or a horse.

The present manufactured medicament can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, e.g., a plasma membrane derived from a human red blood cell. In some embodiments, the nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell.

The present manufactured medicament can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the recipient or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. In another example, the releasable cargo can be a metallic particle, a polymeric particle, a dendrimer particle, or an inorganic particle. In still another example, the releasable cargo can be an agent that facilitates blood supply or transfusion to the recipient. For example, the releasable cargo can be an agent that treats hemolysis or autoimmune reactions such as Rituximab, folate (which is depleted with hemolysis), a corticosteroid, e.g., prednisone, or an iron salt.

The nanoparticle can have any suitable size. For example, the nanoparticle can have a diameter from about 10 nm to about 10 μm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the red blood cell from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the red blood cell from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the donor's red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for facilitating or enabling blood supply or transfusion to the recipient.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35, or 40 hours.

In some embodiments, the outer surface of the nanoparticle can further comprise a synthetic membrane.

In some embodiments, the nanoparticle substantially lacks immunogenicity to the recipient. For example, the cellular membrane can be derived from a red blood cell from the same species of the recipient. In another example, the mammal is a human and the cellular membrane is derived from a human red blood cell.

The present manufactured medicament can further comprise another active ingredient. The other active ingredient can be used for any suitable purposes. In some embodiments, the other active ingredient can be used to facilitate or enable blood supply or transfusion to the recipient. For example, the other active ingredient can be used to treat, prevent or manage the hemolysis associated with an acute hemolytic transfusion reaction (AHTR) in the recipient. In another example, the other active ingredient can be used to treat, prevent or manage the hemolysis associated with a delayed hemolytic reaction in the recipient. In still another example, the other active ingredient can be used to treat, prevent or manage hemolysis or autoimmune reactions, such as Rituximab, folate (which is depleted with hemolysis), a corticosteroid, e.g., prednisone, or an iron salt. In other embodiments, the other active ingredient can be used to treat or prevent a disease or condition in the recipient, e.g., a disease or condition unrelated to the blood supply or transfusion to the recipient.

In some embodiments, the present manufactured medicament can further comprise a pharmaceutically acceptable carrier or excipient.

The present manufactured medicament comprising the nanoparticle can be administered using any suitable delivery mechanisms or techniques. In some embodiments, the present manufactured medicament can be administered alone. In other embodiments, the present manufactured medicament can be administered with a pharmaceutically acceptable carrier or excipient. In still other embodiments, the present manufactured medicament can be administered via a medicament delivery system.

The present manufactured medicament comprising the nanoparticle, alone or in combination with other active ingredient(s), can be administered via any suitable administration routes. In some embodiments, the present manufactured medicament, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

D. Combinations for Supplying a Blood Source to a Recipient

In still another aspect, the present invention provides for a combination for supplying a blood source to a recipient, which combination comprises an effective amount of a nanoparticle and an effective amount of a blood source comprising red blood cells from a donor source, wherein the blood type of said recipient is unknown before receiving said blood source that potentially has a mis-matched blood type, or the blood type of said recipient is known and is a mis-match to the blood type of said blood source, said nanoparticle comprises a) an inner core comprising a noncellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient, and said effective amount of a nanoparticle is configured to be supplied to said recipient before, during, or after said blood source is supplied to said recipient.

The present combination can be made, stored and/or used in any suitable formulation. In some embodiments, the present invention provides for a pharmaceutical composition comprising the above combination admixed with at least one pharmaceutically acceptable carrier or excipient. In other embodiments, the present invention provides for a method for supplying a blood source to a recipient, which method comprise supplying, to a recipient in need of receiving a blood source comprising red blood cells from a donor source, an effective amount of the above combination or pharmaceutical composition.

The above combination or pharmaceutical composition can be used for supplying any suitable types of blood source to a recipient. In some embodiments, the blood source can comprise whole blood from a donor source. In other embodiments, the blood source can comprise red blood cells from a donor source and the white blood cells, clotting factors and/or platelets from the donor source can be removed. In still other embodiments, the blood source can comprise isolated red blood cells from a donor source.

The above combination or pharmaceutical composition can be used for supplying a blood source from any suitable donor to any suitable recipient. In some embodiments, the recipient and the donor can be from different species and the cellular membrane of the nanoparticle can be derived from a red blood cell of a subject that is the same species of the donor. For example, the recipient is a human and the donor is a non-human animal, e.g., a non-human mammal, and the cellular membrane of the nanoparticle is derived from a red blood cell of a subject that is the same species of the non-human animal, e.g., the non-human mammal. In another example, the recipient is a non-human animal, e.g., a first non-human mammal, and the donor is another species of non-human animal, e.g., a second, different species of non-human mammal, and the cellular membrane of the nanoparticle is derived from a red blood cell of a subject that is the same species of the second, different species of non-human mammal.

In other embodiments, the recipient and the donor can be from the same species, and the cellular membrane of the nanoparticle can be derived from a red blood cell of a subject that is the same species of the recipient and the donor. For example, the recipient is a first human and the donor is a second human, and the cellular membrane of the nanoparticle is derived from a red blood cell of a human, e.g., the second human. In another example, the recipient is a non-human animal, e.g., a non-human mammal, the donor is the same species of the non-human animal, and the cellular membrane of the nanoparticle is derived from a red blood cell of a subject that is the same species of the non-human animal.

The above combination or pharmaceutical composition can be used for supplying a blood source to a recipient via any suitable routes or methods. In some embodiments, the above combination or pharmaceutical composition can be used for supplying a blood source to a recipient's circulation intravenously.

The above combination or pharmaceutical composition can be used in any suitable way to facilitate or enable supplying a blood source to a recipient. In some embodiments, the blood type of the recipient can be unknown before receiving the blood source that potentially has a mis-matched blood type. This may be the case when it is impossible or impractical to determine the blood type of a recipient before a blood source has to be supplied to the recipient. For example, in some cases, a recipient is in a medical emergency or other life-threatening situation and there is not enough time for determining the blood type of the recipient before a blood source has to be supplied to the recipient. In another example, a recipient is in an environment wherein there is no tools ore reagents needed to determine the blood type of a recipient before a blood source has to be supplied to the recipient.

In some embodiments, the blood type of the recipient is known and there is a mis-match to the blood type of the blood source. For example, a recipient is in a medical emergency or other life-threatening situation and a blood source with the matching blood type is not available, or not available at a sufficient amount or volume. In this case, a blood source with the mis-matching blood type has to be supplied to the recipient.

The above combination or pharmaceutical composition comprising the nanoparticle can be supplied to a recipient at any suitable time relative to the time when the blood source is supplied to the recipient. In some embodiments, the above combination or pharmaceutical composition comprising the nanoparticle can be supplied to a recipient before the blood source is supplied to the recipient. In other embodiments, the above combination or pharmaceutical composition comprising the nanoparticle can be supplied to a recipient during the time when the blood source is supplied to the recipient. In still other embodiments, the above combination or pharmaceutical composition comprising the nanoparticle can be supplied to a recipient after the blood source is supplied to the recipient.

The cellular membrane of the nanoparticle in the above combination or pharmaceutical composition can comprise any suitable blood type antigen that is missing or potentially missing on red blood cells of the recipient. In some embodiments, the cellular membrane of the nanoparticle can comprise a blood type antigen in a major blood group system that is missing or potentially missing on red blood cells of the recipient. For example, the major blood group system can be the ABO blood group system and the blood type antigen can be the antigen that determines the A blood type, B blood type or AB blood type. In another example, the major blood group system can be the Rh blood group system. In still another example, the blood type antigen that is missing or potentially missing on red blood cells of the recipient can be antigen D, C, c, E, or e. In other embodiments, the cellular membrane of the nanoparticle can comprise a blood type antigen in a minor or rare blood group system that is missing or potentially missing on red blood cells of the recipient.

In some embodiments, the cellular membrane of the nanoparticle in the above combination or pharmaceutical composition comprises a blood type antigen in a blood group system including ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, At$^a$ Antigen, AnWj antigen, Sd$^a$ Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. The above combination or pharmaceutical composition comprising the nanoparticles can be used to enable blood supply or transfusion to a recipient whose red blood cells lack or potentially lack the corresponding blood type antigen in a blood group system such as the ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, At$^a$ Antigen, AnWj antigen, Sd$^a$ Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. For example, the red blood cells of the recipient lack or potentially lack the Vel antigen and the cellular membrane of the nanoparticle comprises the Vel antigen. In some embodiments, the cellular membrane of the nanoparticle comprises a blood type antigen in a blood group system listed in the Table 1 set forth in the above Section IV.B.

The present combination or pharmaceutical composition can be used in any suitable manner or for any suitable purpose. In some embodiments, the present above combination or pharmaceutical composition can be used to supply a blood source to a recipient when the blood type of the recipient is unknown and it is impractical or impossible to determine the blood type of the recipient before supplying the blood source that potentially has a mis-matched blood type. In other embodiments, the present above combination or pharmaceutical composition can be used to supply a blood source to a recipient when the blood type of the recipient is known and the blood source that has a mis-matched blood type is supplied to the recipient because there is not sufficient supply of a blood source that has a matched blood type.

The present above combination or pharmaceutical composition can be used to minimize or prevent an immunologic reaction of the recipient against the red blood cells from the donor source. In some embodiments, the present above combination or pharmaceutical composition can be used to minimize or prevent an immunologic reaction of the recipient against the red blood cells from the donor source that is mediated by the antibodies of the recipient against the red blood cells from the donor source. In other embodiments, the present above combination or pharmaceutical composition can be used to minimize or prevent hemolysis in the recipient due to supplying the blood source that has a mis-matched blood type to the recipient. For example, the present above combination or pharmaceutical composition can be used to minimize or prevent hemolysis that is associated with an acute hemolytic transfusion reaction (AHTR). In another example, the present above combination or pharmaceutical composition can be used to minimize or prevent hemolysis that is associated with a delayed hemolytic reaction.

The present above combination or pharmaceutical composition can be used to supply a blood source to a recipient when the recipient's hemoglobin level indicates that it is necessary or desirable to supply a blood source to a recipient. In some embodiments, the present above combination or pharmaceutical composition can be used to supply a blood source to a recipient when the recipient's hemoglobin level falls below about 10 g/dL or hematocrit falls below about 30%. In other embodiments, the present above combination or pharmaceutical composition can be used to supply a blood source to a recipient when the recipient's hemoglobin level falls below about 7-8 g/dL.

The present above combination or pharmaceutical composition can be used to supply a blood source to any suitable recipient. In some embodiments, the recipient can be a pediatric patient, a pregnant woman, a person with massive trauma, a person who needs massive blood transfusion, a person who needs frequent blood transfusion, a person with a medical emergency, a person in a surgical procedure, a person in a war zone, an accident, a remote area, an epidemic, or a pandemic. In other embodiments, the present above combination or pharmaceutical composition can be configured for veterinary use. For example, the present above combination or pharmaceutical composition can be used to supply a blood source to a recipient that is a pet, a farm animal or an economic animal. In another example, the present above combination or pharmaceutical composition can be used to supply a blood source to a recipient that is a cat, a cattle, a dog, a pig or a horse.

The present above combination or pharmaceutical composition can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, e.g., a plasma membrane derived from a human red blood cell. In some embodiments, the nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell.

The present combination or pharmaceutical composition can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the recipient or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. In another example, the releasable cargo can be a metallic particle, a polymeric particle, a dendrimer particle, or an inorganic particle. In still another example, the releasable cargo can be an agent that facilitates blood supply or transfusion to the recipient. For example, the releasable cargo can be an agent that treats hemolysis or autoimmune reactions such as Rituximab, folate (which is depleted with hemolysis), a corticosteroid, e.g., prednisone, or an iron salt.

The nanoparticle can have any suitable size. For example, the nanoparticle can have a diameter from about 10 nm to about 10 µm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the red blood cell from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the red blood cell from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the donor's red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for facilitating or enabling blood supply or transfusion to the recipient.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35, or 40 hours.

In some embodiments, the outer surface of the nanoparticle can further comprise a synthetic membrane.

In some embodiments, the cellular membrane can be derived from a red blood cell from the same species of the recipient. For example, the recipient is a human and the cellular membrane is derived from a human red blood cell.

The present combination or pharmaceutical composition can further comprise another active ingredient. The other active ingredient can be used for any suitable purposes. In some embodiments, the other active ingredient can be used to facilitate or enable blood supply or transfusion to the recipient. For example, the other active ingredient can be used to treat, prevent or manage the hemolysis associated with an acute hemolytic transfusion reaction (AHTR) in the recipient. In another example, the other active ingredient can be used to treat, prevent or manage the hemolysis associated with a delayed hemolytic reaction in the recipient. In still another example, the other active ingredient can be used to treat, prevent or manage hemolysis or autoimmune reactions, such as Rituximab, folate (which is depleted with hemolysis), a corticosteroid, e.g., prednisone, or an iron salt. In other embodiments, the other active ingredient can be used to treat or prevent a disease or condition in the recipient, e.g., a disease or condition unrelated to the blood supply or transfusion to the recipient.

In some embodiments, the present combination or pharmaceutical composition can further comprise a pharmaceutically acceptable carrier or excipient.

The present combination or pharmaceutical composition comprising the nanoparticle can be administered using any suitable delivery mechanisms or techniques. In some embodiments, the present combination or pharmaceutical composition can be administered alone. In other embodiments, the present combination or pharmaceutical composition can be administered with a pharmaceutically acceptable carrier or excipient. In still other embodiments, the present combination or pharmaceutical composition can be administered via a medicament delivery system.

The present combination or pharmaceutical composition comprising the nanoparticle, alone or in combination with other active ingredient(s), can be administered via any suitable administration routes. In some embodiments, the present combination or pharmaceutical composition, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

E. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl mono stearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

One of ordinary skill in the art may modify the formulations within the teachings of the specification to provide numerous formulations for a particular route of administration. In particular, the nanoparticles, alone or in combination with other active ingredient(s), may be modified to render them more soluble in water or other vehicle. It is also well within the ordinary skill of the art to modify the route of administration and dosage regimen of a particular nanoparticle, alone or in combination with other active ingredient(s), in order to manage the pharmacokinetics of the present compounds for maximum beneficial effect in a patient.

F. Exemplary Embodiments

The most well-known blood group antigens include A, B, O giving rise to A, AB, B and O blood types; each of these can then be Rh "positive" or "negative", giving rise to eight possible combinations. These categorizations are the most relevant in the majority of situations, and help prevent the most common transfusion reactions. However, there are actually at least 33 major blood group antigens (and approximately 200 minor antigen groups) of which at about 20 (such as Kell, c, E, Vel, etc.) have the capability of causing transfusion reactions. It is currently impractical to screen for these antigens in donors or recipients.

When a person does not possess a certain antigen on their own red blood cells (RBCs), the plasma will often contain naturally-occurring antibodies to the missing antigen. These antibodies appear in the blood as early as infancy or early childhood.

In order to detect potentially missed transfusion incompatibilities, blood "cross-matching" is done prior to the actual transfusion of donor blood, if time allows. Typically performed in a laboratory by a certified laboratory technologist, there are several cross-matching methods but one of the more comprehensive methods involves a sample of donor blood is mixed with patient plasma or serum to check if agglutination is observed (indicating incompatibility). This process usually takes approximately one hour. Given the time urgency in emergency situations, however, complete cross-matching is not always practical, and "ABO" compatible blood that is Rh matched is given empirically, or another more abbreviated but less comprehensive test can be done.

In the cases of patients with certain rare blood types, there are further difficulties introduced. There are situations where a patient with a certain blood type cannot be cross-matched with any available donor blood. This difficulty is compounded by the fact that most donor blood is not analyzed for antigen types beyond the major categories (A, B, O, Rh+/−). There exist registries of rare blood donors (such as the American Rare Donor Program and the International Blood Group Reference Laboratory in Bristol, England), but there are few active donors for certain rare blood types, such as Vel. In such circumstances, the patient must go without blood, or the clinician must weigh the cost/benefit of purposely transfusing cross-match incompatible blood.

As one example, Vel is an antigen that is missing in only 1 out of 2500 individuals of European descent—approximately 200,000 individuals in Europe and 100,000 individuals in North America are Vel negative. However, in the event these patients need a blood transfusion, almost all known donor blood is incompatible. Even in a situation where a donor could be identified, many medical procedures or traumas can necessitate dozens or even up to 100 units of blood over the course of a hospitalization, which could overwhelm any scare supply of cross-matched blood.

A solution for this problem involves the utilization of exemplary RBC coated nanoparticles. Such exemplary RBC coated nanoparticles can have a biocompatible and biodegradable core coated with RBC membranes expressing certain antigens expressed in mismatched donor blood. The exemplary RBC coated nanoparticles, administered before, during, or after mismatched donor blood infusion, can serve as decoys to safely absorb and/or bind to pre-formed antibodies in the patient against such antigens; the antibodies would attack the exemplary RBC coated nanoparticles instead of the donor RBCs. The decoy strategy can prevent or reduce hemolysis of the donor RBCs and the many sequelae that usually result from such hemolysis, which include, but are not limited to loss of oxygen carrying capacity of donor blood, kidney damage, metabolic alkalosis (from conversion of citrate in RBCs to bicarbonate), hemochromatosis, hyperbilirubinemia, and others.

As a specific example, patients with Vel− blood type will have difficulty accessing Vel− donor blood supply. In such a case that warranted the administration of known mismatched Vel+ blood, a Vel− patient could receive a dose of "A/B/O/Rh" compatible exemplary RBC coated nanoparticles that are Vel+. The A/B/O/Rh compatible exemplary RBC coated nanoparticles (for instance O− blood) are not expected to unduly elicit additional immune responses from the recipient, but the Vel+ antigens are expected to bind to the anti-Vel antibodies in the patient, thus removing them from being able to attack donor RBCs. As the exemplary RBC coated nanoparticles have a solid core, there is no hemolysis resulting from direct binding of such antibodies. The exemplary RBC coated nanoparticles, with the attached antibodies are then processed, metabolized, and excreted (via a now presumed hepatic route), thus safely removing said anti-Vel antibodies. Moreover, the exemplary RBC coated nanoparticles have sizes and dimensions significantly smaller than RBCs (e.g., about 3,000 N exemplary RBC coated nanoparticles to 1 RBC) such that even if there is cross-binding and agglutination of multiple exemplary RBC coated nanoparticles, the size of resulting clusters would be less likely to obstruct blood flow or cause hemodynamic instability as much as similarly agglutinated RBCs.

The following includes other RBC antigens that are also often implicated in transfusion reactions, although the list is not exhaustive, and new RBC surface antigens are still anticipated to be discovered in the future which would be amenable to the same stated strategy. Also, many of these antigens are almost universally present on most individuals' RBCs, but for rare patients missing these, transfusion reactions become a potential hazard. The exemplary RBC coated nanoparticles can be used to enable or facilitate blood supply or transfusion to subjects or patients whose RBCs lack these antigens. For example, Duffy antigen/chemokine receptor (DARC) is a glycosylated membrane protein also known as Fy glycoprotein or CD234 and is a encoded by the DARC gene; many patients with African ancestry are Duffy−, whereas Duffy− is rare in many parts of the world. Other exemplary rare RBC surface antigens include $Er^a$ and a (<1%) rare antigen, $Er^b$, Lan antigen, $At^a$ Antigen that is only found in people of African descent, AnWj antigen associated with severe hemolytic transfusion reactions, and $Sd^a$ Antigen. The exemplary RBC coated nanoparticles can also be used to enable or facilitate blood supply or transfusion to subjects or patients whose RBC misses the following rare surface antigens: Batty (By), Biles (Bi), Box ($Bx^a$), Christiansen ($Chr^a$), HJK, HOFM, JFV, JONES, Jensen ($Je^a$), Katagiri (Kg), Livesay ($Li^a$), Milne, Oldeide ($Ol^a$), Peters ($Pt^a$), Rasmussen (RASM), Reid ($Re^a$), REIT, SARA, Torkildsen ($To^a$) and Bg (Bennett-Goodspeed).

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for supplying a blood source to a recipient, which method comprise supplying a blood source comprising red blood cells from a donor source to a recipient in need of said supplied blood source, wherein:
the blood type of said recipient is unknown before receiving said blood source that potentially has a mis-matched blood type, or the blood type of said recipient is known and is a mis-match to the blood type of said blood source, and
before, during, or after supplying said blood source to said recipient, supplying to said recipient an effective amount of a nanoparticle comprising a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient.

2. The method of claim 1, wherein the blood source comprises:
a) whole blood from a donor source;
b) red blood cells from a donor source and the white blood cells, clotting factors and/or platelets from the donor source are removed; or
c) isolated red blood cells from a donor source.

3. The method of claim 1, wherein the recipient and the donor are from the different species and the cellular membrane of the nanoparticle is derived from a red blood cell of a subject that is the same species of the donor.

4. The method of claim 1, wherein the recipient and the donor are from the same species, and the cellular membrane of the nanoparticle is derived from a red blood cell of a subject that is the same species of the recipient and the donor.

5. The method of claim 1, wherein the blood source is supplied to the recipient's circulation intravenously.

6. The method of claim 1, wherein the blood type of the recipient:
a) is unknown before receiving the blood source that potentially has a mis-matched blood type; or
b) is known and there is a mis-match to the blood type of the blood source.

7. The method of claim 1, which comprises:
a) supplying an effective amount of the nanoparticle to the recipient before supplying the blood source to the recipient;
b) supplying an effective amount of the nanoparticle to the recipient during supplying the blood source to the recipient; or
c) supplying an effective amount of the nanoparticle to the recipient after supplying the blood source to the recipient.

8. The method of claim 1, wherein the cellular membrane of the nanoparticle comprises:
a) blood type antigen in a major blood group system that is missing or potentially missing on red blood cells of the recipient; or
b) a blood type antigen in a minor or rare blood group system that is missing or potentially missing on red blood cells of the recipient.

9. The method of claim 1, wherein the cellular membrane of the nanoparticle comprises a blood type antigen in a blood group system selected from the group consisting of ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, $At^a$ Antigen, AnWj antigen, $Sd^a$ Antigen, Batty (By), Biles (Bi), Box ($Bx^a$), Christiansen ($Chr^a$), HJK, HOFM, JFV, JONES, Jensen ($Je^a$), Katagiri (Kg), Livesay ($Li^a$), Milne, Oldeide ($Ol^a$), Peters ($Pt^a$), Rasmussen (RASM), Reid ($Re^a$), REIT, SARA, Torkildsen ($To^a$) and Bg (Bennett-Goodspeed).

10. The method of claim 1, wherein the red blood cells of the recipient lack or potentially lack a blood type antigen in a blood group system selected from the group consisting of ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, $At^a$ Antigen, AnWj antigen, $Sd^a$ Antigen, Batty (By), Biles (Bi), Box ($Bx^a$), Christiansen ($Chr^a$), HJK, HOFM, JFV, JONES, Jensen ($Je^a$), Katagiri (Kg), Livesay ($Li^a$), Milne, Oldeide ($Ol^a$), Peters ($Pt^a$), Rasmussen (RASM), Reid ($Re^a$), REIT, SARA, Torkildsen ($To^a$) and Bg (Bennett-Goodspeed).

11. The method of claim 1, wherein the red blood cells of the recipient lack or potentially lack the Vel antigen and the cellular membrane of the nanoparticle comprises the Vel antigen.

12. The method of claim 1, wherein the blood type of the recipient is unknown and it is impractical or impossible to determine the blood type of the recipient before supplying the blood source that potentially has a mis-matched blood type.

13. The method of claim 1, wherein the blood type of the recipient is known and the blood source that has a mis-matched blood type is supplied to the recipient because there is not sufficient supply of a blood source that has a matched blood type.

14. The method of claim 1, which is used to minimize or prevent hemolysis in the recipient due to supplying the blood source that has a mis-matched blood type to the recipient.

15. The method of claim 1, which is used for supplying a blood source to a recipient when the recipient's hemoglobin level falls below about 10 g/dL or hematocrit falls below about 30%.

16. The method of claim 1, which further comprises conducting a blood type compatibility test between a blood sample of the recipient and the blood source in the presence and absence of the nanoparticle to assess the efficacy of the nanoparticle for minimizing or preventing an immunologic reaction of the recipient against the red blood cells from the donor source.

17. The method of claim 1, wherein the blood type of the recipient is unknown and further comprises, after supplying the blood source to the recipient, conducting a blood type compatibility test between a blood sample of the recipient and the blood source to assess whether the blood type of the recipient matches with the blood type of the blood source.

18. The method of claim 1, wherein the recipient is a pediatric patient, a pregnant woman, a person with massive trauma, a person who needs massive blood transfusion, a person who needs frequent blood transfusion, a person with a medical emergency, a person in a surgical procedure, a person in a war zone, an accident, a remote area, an epidemic, or a pandemic.

19. The method of claim 1, wherein the cellular membrane comprises a plasma membrane derived from a red blood cell.

20. A combination for supplying a blood source to a recipient, which combination comprises an effective amount of a nanoparticle and an effective amount of a blood source comprising red blood cells from a donor source, wherein
   the blood type of said recipient is unknown before receiving said blood source that potentially has a mis-matched blood type, or the blood type of said recipient is known and is a mis-match to the blood type of said blood source,
   said nanoparticle comprises a) an inner core comprising a non-cellular material, and b) an outer surface comprising a cellular membrane derived from a red blood cell, said cellular membrane of said nanoparticle comprising a blood type antigen that exists on said red blood cell from said donor source, but is missing or potentially missing on red blood cells of said recipient, and
   said effective amount of a nanoparticle is configured to be supplied to said recipient before, during, or after said blood source is supplied to said recipient.

21. A method for supplying a blood source to a recipient, which method comprise supplying, to a recipient in need of receiving a blood source comprising red blood cells from a donor source, an effective amount of a combination of claim 20.

* * * * *